Feb. 22, 1949. H. C. SWIM Plant Pat. 829
ROSE PLANT
Filed June 24, 1947
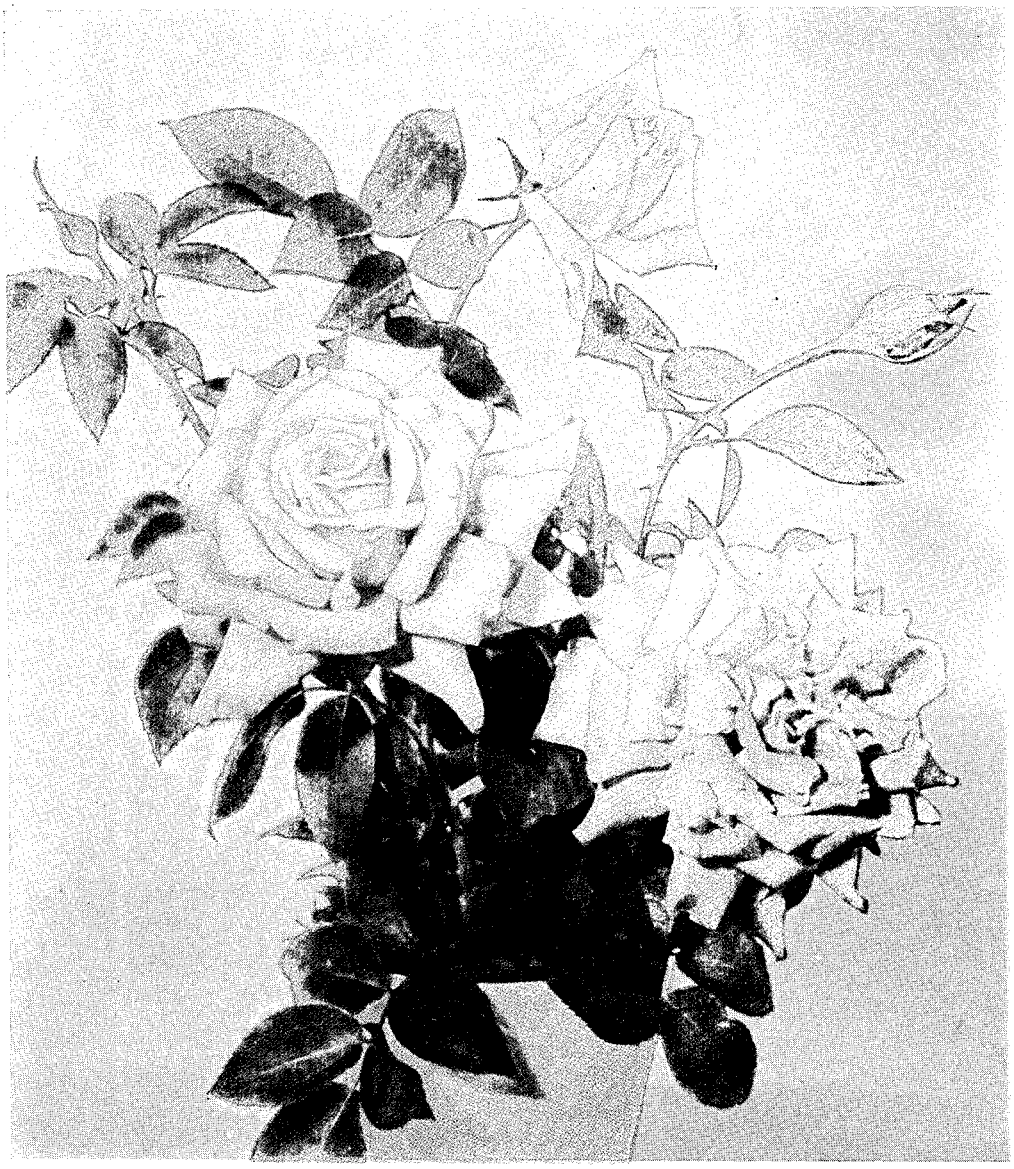
Inventor
H. C. Swim
By Robert Robb
Attorney Patented Feb. 22, 1949

Plant Pat. 829

UNITED STATES PATENT OFFICE

829

ROSE PLANT

Herbert C. Swim, Ontario, Calif., assignor to Armstrong Nurseries, Inc., Ontario, Calif., a corporation of California Application June 24, 1947, Serial No. 756,589

1 Claim. (Cl. 47—61)

The present invention relates to a new and distinct variety of Hybrid Tea Rose plant, resulting from the cross of the known varieties "Contrast" × "Charlotte Armstrong," and possessing a combination of characteristics differing, so far as I am aware, from any other rose known to commerce.

The novel characteristics of this new variety are found in the plant structure, habits of growth, and particularly in the flowers, speaking with reference to color, size, petalage and form as these vary during the periods of blooming from early spring to fall. These novel characteristics may be concisely stated as follows:

(1) A vigorous, upright, free-branching plant, abundantly furnished with large leaves that are highly resistant to mildew.

(2) Flowers in a color substantially as described and illustrated herein and with a size characteristically varying from very large in early spring to medium-small in mid-summer to medium in the fall, and with the number of petals varying more or less in proportion to the size of the flower, being extremely double in the early spring, merely double in the summer, and very double in the fall, but with not as many petals in the fall bloom as in the spring.

Since the novel characteristics above referred to are not found in any prior rose, their distinctiveness may best be understood by a careful comparison with each of its parents as now set forth.

This new variety of rose has only one minor point of resemblance to its seed parent, "Contrast" (unpatented). Both this new variety and "Contrast" are upright in habit but this new variety is not as tall and rangy as its seed parent, but is lower growing, more bushy and free-branched. This new variety has a distinctly different color of flower and different shape, and a different texture of the leaves which are more highly resistant to mildew than those of "Contrast." The texture of the leaves of this new variety is properly classified as heavy to leathery and semi-glossy, whereas the leaves of "Contrast" are more properly classified as soft and glossy. This new variety is characterized by a large number of moderately large, and a large number of small thorns, whereas "Contrast" has relatively few, but large thorns. While the color pattern is very different in this new variety from that of "Contrast," it nevertheless obviously inherited some of the brilliance from the color of the flower of its seed parent.

Since the well known variety, "Charlotte Armstrong" (Pl. Pat. #455), was used as a pollen parent because of its many excellent qualities, and the seedlings resulting from the cross of "Contrast" × "Charlotte Armstrong" were selected on the basis of their complement of some of these characteristics, this new variety has some slight resemblances to its pollen parent. The leaves of these two varieties are similar in their resistance to mildew and in their texture. The leaves of this new variety, however, are larger than those of "Charlotte Armstrong" with a greater proportion of width to length. The plants of this new variety are somewhat more abundantly furnished with leaves than the plants of "Charlotte Armstrong." The size and pattern of the thorns in this new variety is very similar to that of "Charlotte Armstrong." On the other hand, the habit of the plant is quite different from that of "Charlotte Armstrong," being characteristically bushy and upright whereas plants of "Charlotte Armstrong" are characteristically more open and rangy in habit and could more appropriately be described as upright-spreading. The color of the flower of this new variety is quite distinct from that of "Charlotte Armstrong," being characterized by containing both more yellow and red pigment than is found in the flowers of its pollen parent. The flowers of "Charlotte Armstrong" are characterized by 25 to 35 petals whereas this new variety averages 30 to 45 petals in the flowers. Both of the varieties are characterized by a slight but spicy fragrance. The buds of "Charlotte Armstrong" are longer and more stream-lined than those of this new variety as is consistent with the somewhat fewer number of petals to be found in "Charlotte Armstrong." Many more petaloids are to be found in this new variety than in its pollen parent.

Asexual reproduction of this new variety shows the foregoing characteristics come true to form and are established.

The accompanying drawing shows specimens of the flowers at the various stages of development, depicting as nearly as possible the color range at said stages, and also specimens of the foliage in its various stages of development.

The following is a detailed description of the new variety, color terminology being in accordance with Robert F. Wilson's Horticultural Colour Chart with exceptions noted from Ridgway's Color Standards and Nomenclature:

Type: Hardiness untested; bush; outdoor; seedling; for cut flowers and garden decoration.

Class: Hybrid tea.

Breeding: Seedling.

*Seed parent.*—"Contrast."

*Pollen parent.*—"Charlotte Armstrong."

Propagation: Holds its distinguishing characteristics through succeeding propagations by budding.

*Flower*

Locality Where Grown: Ontario, California.
Date of Observations: November 1, 1946, at Ontario, Cal.
Flowers Borne: Singly, sometimes two or more, to stem; in irregular cluster; on normal medium-length stems.
Quantity of bloom: Abundant; outdoors.
Continuity: Continuous during growing season.
Fragrance: Slight; spicy.
Bud:
*Peduncle.*—Medium to long; medium caliper; erect; medium rough; numerous gland-tipped cilia and prickles. *Color*—near Rainette Green, Plate XXXI (Ridgway).
*Before calyx breaks.*—*Size*—medium. *Form*—long; pointed; with foliaceous appendages, gland-tipped cilia and glandular bloom on the surface of the bud; with slender, much cut foliaceous parts extending beyond the tip of the bud equal to ¾ or more of its length.
*As calyx breaks.*—*Color*—near Chrysanthemum Crimson, Plate 824/2, page 169. *Sepals*—inner surface with fine, woolly tomentum; When the margin of a sepal is not covered by the margin of an adjacent sepal, it has woolly tomentum and stipitate glands on both margins; but if margin is covered with adjacent sepals, margin has only woolly tomentum.
*As first petal opens.*—*Size*—large. *Form*—medium to long; pointed. *Color*—outside: Crimson, Plate 22/1, page 22, shading through Geranium Lake, Plate 20/1, page 20, to a blotch of Lemon Yellow, Plate 4/2, page 4, at base of petal; inside—Crimson, Plate 22, page 22, shading to a blotch of Lemon Yellow, Plate 4/2, page 4, at base of petal.
*Opening.*—Opens up well.
Bloom: Size, when fully open—usually large; 4" to 4½".
*Petalage.*—Usually very double; from 30 to 45 petals plus 15 to 30 petaloids, arranged more or less regularly.
*Form.*—Very full, high center at first and remaining high centered; petals remaining at first very loosely rolled outward; becoming later, at maturity, tightly rolled outward.
Petals: Thick to leathery; with inside velvety and outside satiny.
*Shape.*—Outside: obovate; intermediate: obovate-cuneate with one notch; inside: obovate-cuneate with one notch.
*Color.*—Colors may be modified by being shaded, washed with other colors.

This description of a newly opened flower was made from a rose grown outdoors in the month of September, at Ontario, California:

*Color.*—*Outside petal*—outside surface: Rose Madder, Plate 23/2, page 23, with a spot of Aureolin, Plate 3/1, page 3, at base of petal; inside surface: Rose Madder, Plate 23/1, page 23, with a spot of Aureolin, Plate 3/2, shading to Aureolin, Plate 3/1, page 3, at base of petal. *Intermediate petal*—outside surface: Rose Madder, Plate 23/2, page 23, with a spot of Aureolin, Plate 3/1, page 3, at base of petal; inside surface: Rose Madder, Plate 23/1, page 23, with a narrow outer margin of Rose Madder, Plate 23/3, page 23, with a spot of Aureolin, Plate 3/1, page 3, at base of petal. *Inner petal*—outside surface: Crimson, Plate 22/1, page 22, with a spot of Aureolin, Plate 3/2, page 3, at base of petal; inside surface: Crimson, Plate 22, page 22, with a spot of Aureolin, Plate 3/2, page 3, at base of petal.

This description was made from a rose that was open for three days outdoors in September, at Ontario, California:

*Color.*—*Outside petal*—outside surface: Neyron Rose, Plate 623, page 76, with a spot of Aureolin, Plate 3/2, page 3, at base of petal; inside surface: Rose Madder, Plate 23/1, page 23, with a spot of Aureolin, Plate 3/1, page 3, at base of petal. *Inside petal*—outside surface: Rose Madder, Plate 23/1, page 23, with a spot of Aureolin, Plate 3/1, page 3, at base of petal; inside surface: Rose Madder, Plate 23, page 23, with a spot of Aureolin, Plate 3/1, page 3, at base of petal.
*General color effect.*—Newly opened flower—Rose Madder, Plate 23/1, page 23. Three days open—near Rose Madder, Plate 23/1, page 23.
*Behavior.*—Drop off cleanly; affected by hot, dry weather by only a very slight variation in color.
*Flower longevity.*—On bush in garden, three days in September. Cut roses grown outdoors kept at living-room temperatures, 2 to 3 days in September. Untried for greenhouse growing.

*Reproductive organs*

Stamens: Medium number, arranged irregularly about pistils.
Filaments: Medium length; 6 to 10 mm. long. *Color*—Lemon Yellow, Plate 4, page 4. Most with anthers.
Anthers: Medium size; all open at once. *Color*—Saffron Yellow, Plate 7/1, page 7.
Pollen: Moderate. *Color*—Yellow Ochre, Plate 07, page 101.
Pistils: Many, approximately 80 to 90 in number.
Styles: Uneven; medium length; thin; loosely separated; 7–9 mm. in length. *Color*—Crimson, Plate 22, page 22, at upper end shading to Uranium Green, Plate 63/2, page 63.
Stigma: Near Lemon Yellow, Plate 4/3, page 4, translucent.
Ovaries: All enclosed in calyx.
Hips: This variety very seldom sets hips under usual outdoor growing conditions.
Sepals: Permanent; moderately long; recurved. *Color*—inside: near Light Lumiere Green, Plate XVII (Ridgway); outside: near Light Elm Green, Plate XVII (Ridgway).

*Plant*

Foliage:
*Leaves.*—Compound of five to seven leaflets; abundant; medium to large; heavy to leathery; semi-glossy.
*Leaflets.*—Shape—oblong, lanceolate, with apex acute, base obtuse; margin doubly serrate.
*Color.*—*Mature*—upper surface: near Leaf Green, Plate XLI (Ridgway); under surface: near Asphodel Green, Plate XLI (Ridgway). *Young*—upper surface: Bice Green, Plate XVII, (Ridgway), washed with near Burnt Lake, Plate XII (Ridgway); under surface: Light Bice Green Plate XVII (Ridgway), washed with Indian Red, Plate XXVII (Ridgway).

*Rachis.*—Medium heavy. Upper side — grooves with a few stipitate glands on edges; under side—moderately prickly with few stipitate glands.

*Stipules.*—Average length; average width; with moderately long points, turning out at an angle of less than 90°.

*Disease.*—Resistant to mildew.

Growth:

*Habit.*—Bushy; upright; much branched.

*Growth.*—Vigorous.

*Canes.*—Average caliper.

*Main stems.*—*Color*—light Cress Green, Plate XXXI (Ridgway), with stripes of callus formed by splitting of epidermal bark layer of near Verona Brown, Plate XXIX (Ridgway). *Large prickles*—many; medium length; occasionally straight, usually hooked slightly downward; with short narrow base. Color—near Chestnut, Plate II (Ridgway). *Small prickles* — several. Color—near Chestnut, Plate II (Ridgway). *Hairs*—none.

*Branches.* Color—Bice Green, Plate XVII (Ridgway). *Large prickles*—many; medium length; occasionally straight, usually hooked slightly downward; with short narrow base. Color—Olive Ocher, Plate XXX (Ridgway), shading to near Brussels Brown, Plate III (Ridgway), at tip. *Small prickles* — several. Color — varies from Olive-Ocher, Plate XXX (Ridgway) to Rood's Brown, Plate XXVIII (Ridgway). *Hairs*—none.

*New shoots.* Color—Grape Green, Plate XLI (Ridgway). *Large prickles*—many; medium length; occasionally straight, usually hooked slightly downward; with short narrow base. Color—near Vinacious-Russet, Plate XXVIII (Ridgway) to near Lime Green, Plate XXXI (Ridgway), at tip. *Small prickles.* — Several. Color — near Vinacious-Russet, Plate XXVIII, (Ridgway) to near Lime Green, Plate XXXI (Ridgway), at tip. *Hairs*—none.

I claim:

A new and distinct variety of rose plant characterized as to novelty by the vigorous, upright, free-branching habits of growth of the plant, abundantly furnished with large leaves highly resistant to mildew; by the color of its flowers and the size thereof characteristically varying from very large in early spring to medium-small in mid-summer to medium in the fall, and with the number varying more or less in proportion to the size of the flower—extremely double in the early spring, merely double in the summer, and very double in the fall, with not so many petals in the fall bloom as in the spring, substantially as shown and described.

HERBERT C. SWIM.

No references cited.